United States Patent
Oliveira Ferreira et al.

(10) Patent No.: US 11,836,921 B2
(45) Date of Patent: Dec. 5, 2023

(54) ARTIFICIAL-INTELLIGENCE-BASED GLOBAL CARDIAC MOTION CLASSIFICATION

(71) Applicant: AI4MEDIMAGING—MEDICAL SOLUTIONS, S.A., Braga (PT)

(72) Inventors: Manuel João Oliveira Ferreira, Povoa de Lanhoso (PT); Eva Carína Alves Costa, Tenões Braga (PT); Nelson Costa Martins, Braga (PT); Vitor Eira Pereira, Barcelos (PT); Bruno Miguel da Silva Barbosa, Frossos Braga (PT); Pedro Miguel Morgado Cabral da Silva, Arvore-Vila do Conde (PT); Ana Luisa Oliveira, Santa Maria da Feira (PT); Mariana Fontainhas Rodrigues, Barcelos (PT); Inés Raquel Oliveira da Silva, Barcelos (PT)

(*) Notice: Subject to any disclaimer, the term of this patent is extended or adjusted under 35 U.S.C. 154(b) by 118 days.

(21) Appl. No.: 17/072,380

(22) Filed: Oct. 16, 2020

(65) Prior Publication Data

US 2021/0125333 A1  Apr. 29, 2021

Related U.S. Application Data

(63) Continuation-in-part of application No. 16/669,360, filed on Oct. 30, 2019.

(30) Foreign Application Priority Data

Oct. 28, 2019  (PT) .......................................... 115867
Oct. 30, 2019  (EP) .................................... 19206156

(51) Int. Cl.
*G06T 7/00* (2017.01)
*G06T 7/11* (2017.01)
(Continued)

(52) U.S. Cl.
CPC .......... *G06T 7/0016* (2013.01); *A61B 5/0044* (2013.01); *A61B 5/055* (2013.01);
(Continued)

(58) Field of Classification Search
CPC ......... G06T 7/0012; G06T 7/11; G06T 7/246; G06T 7/0016; G06T 11/003;
(Continued)

(56) References Cited

U.S. PATENT DOCUMENTS 9,311,703 B2 * 4/2016 Codella .................. G06T 7/168
10,321,892 B2 * 6/2019 Wang ...................... G06T 7/251
(Continued)

OTHER PUBLICATIONS

Avendi et al. A combined deep-learning and deformable model approach to fully automatic segmentation of the left ventrical cardiac MRI, Medical Image Anallysis, May 2016.*
(Continued)

*Primary Examiner* — John B Strege
(74) *Attorney, Agent, or Firm* — Woods Patent Law, P.C.

(57) ABSTRACT

A method for providing a global cardiac wall motion classification for a patient is disclosed, and includes employing Cardiac Magnetic Resonance (CMR) image data. In some embodiments, the method comprises one or more of a myocardium segmentation step, a slice classification step, a movement feature extraction step, and a global classification or evaluation step, wherein a patient is classified as having normal cardiac wall motion, or as having suspicious or abnormal cardiac wall motion.

20 Claims, 14 Drawing Sheets
(10 of 14 Drawing Sheet(s) Filed in Color)

(51) Int. Cl.
  *G06T 7/246* (2017.01)
  *G16H 30/20* (2018.01)
  *G16H 50/20* (2018.01)
  *A61B 5/00* (2006.01)
  *A61B 5/055* (2006.01)
  *A61B 5/11* (2006.01)
  *G06T 11/00* (2006.01)
  *G06F 18/2431* (2023.01)

(52) U.S. Cl.
  CPC .......... *A61B 5/1128* (2013.01); *A61B 5/7267* (2013.01); *G06F 18/2431* (2023.01); *G06T 7/0012* (2013.01); *G06T 7/11* (2017.01); *G06T 7/246* (2017.01); *G06T 11/003* (2013.01); *G16H 30/20* (2018.01); *G16H 50/20* (2018.01); *G06T 2207/10088* (2013.01); *G06T 2207/20084* (2013.01); *G06T 2207/30048* (2013.01)

(58) Field of Classification Search
  CPC . G06T 2207/10088; G06T 2207/20084; G06T 2207/30048; G06T 2207/10016; G06T 2207/20076; G06T 2207/20081; G06T 2200/04; A61B 5/0044; A61B 5/055; A61B 5/1128; A61B 5/7267; G06K 9/628; G06V 10/40; G16H 30/20; G16H 50/20
  See application file for complete search history.

(56) References Cited

U.S. PATENT DOCUMENTS

| | | | |
|---|---|---|---|
| 10,517,564 B2* | 12/2019 | Konofagou | A61B 8/02 |
| 11,361,546 B2* | 6/2022 | Carreira | G06V 40/23 |
| 2016/0061058 A1 | 3/2016 | Young et al. | |
| 2018/0042497 A1* | 2/2018 | Cowan | G01R 33/56308 |
| 2018/0140216 A1* | 5/2018 | Li | A61B 5/02 |
| 2018/0333104 A1* | 11/2018 | Sitek | G06N 5/046 |
| 2020/0046244 A1* | 2/2020 | Alam | A61B 5/349 |
| 2020/0125852 A1* | 4/2020 | Carreira | G06V 20/41 |
| 2021/0085260 A1* | 3/2021 | Schneider | G01R 33/5676 |
| 2021/0350179 A1* | 11/2021 | Bello | G06N 3/0454 |
| 2022/0031218 A1* | 2/2022 | Klein | A61B 5/308 |
| 2022/0215915 A1* | 7/2022 | Lyman | G06F 3/0484 |

OTHER PUBLICATIONS

Moreno Ramon A et al, "A combined deep-teaming approach to foil automatic left ventricle segmentation in cardiac magnetic resonance imaging," Progress in Biomedical Optics and Imaging, SPJE—International Society for R Optical Engineering, Mar. 15, 2019, pp. 109531Y-109531Y, vol. 10953, Bellingham, WA, US.

Chen Chen et al., "Unsupervised Multi-modal style transfer for cardiac MR segmentation," arvix.org, Aug. 20, 2019, XP081466083, Cornell University Library, Cornell University, Ithaca, New York US.

* cited by examiner

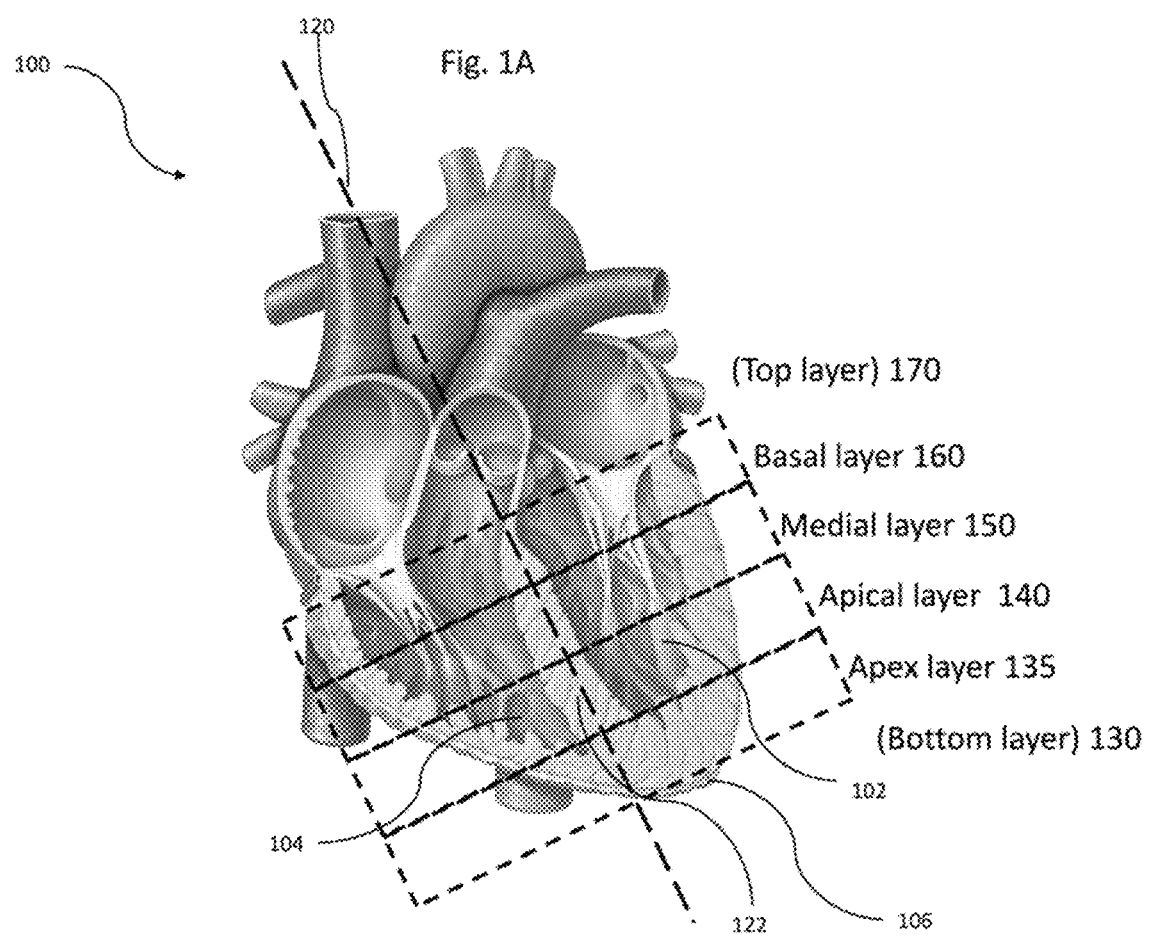

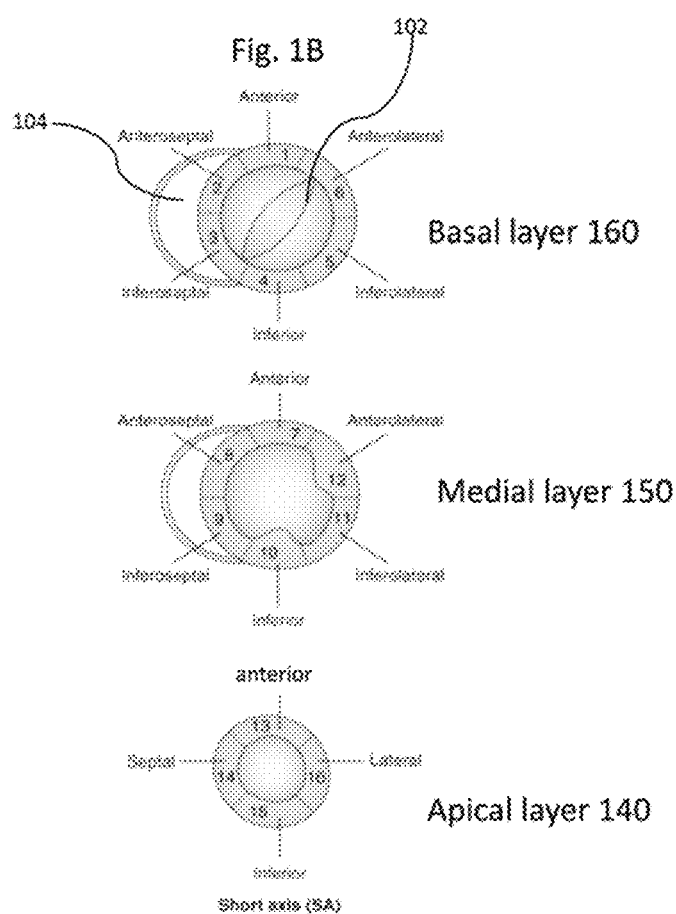
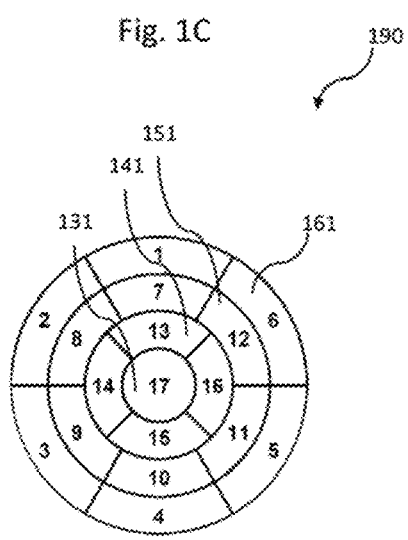

Fig. 9
Dimensionality reduction strategy:
- Convert cartesian coordinates to polar coordinates:
  - From the myocardium mask's centroid, measure the inner and outer radius for all angles from 0° to 360°
- Each frame is reduced to a couple of (r, θ) lines
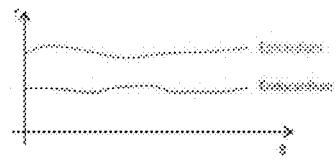
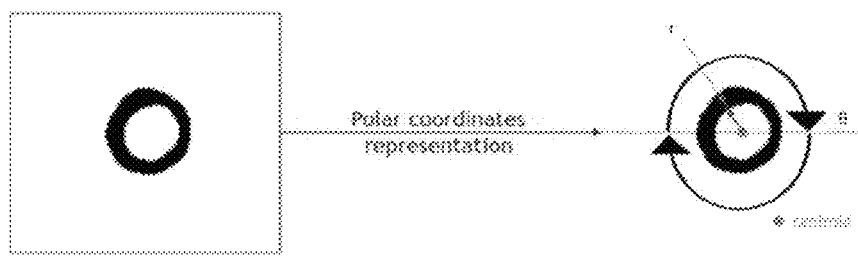

ARTIFICIAL-INTELLIGENCE-BASED GLOBAL CARDIAC MOTION CLASSIFICATION

RELATED APPLICATIONS

This application is a continuation-in-part of U.S. patent application Ser. No. 16/669,360 to Ferreira et al. entitled "Artificial Intelligence Based Cardiac Motion Classification" filed on Oct. 30, 2019 (hereafter "the '360 patent application"). This application further claims priority and other benefits from: (a) the '360 patent application; (b) Portuguese Patent Application No. 115867 filed on Oct. 28, 2019 (hereafter "the 867 patent application"), and (c) European Patent Application EP19206156 filed on Oct. 30, 2019 (hereafter "the '156 patent application"). The '360 patent application is hereby incorporated by reference herein, in its entirety.

FIELD OF THE INVENTION

The present invention relates to the field of cardiac wall motion classification. In particular, the present invention is directed to a computer-implemented method and an apparatus for using artificial intelligence (AI) in classifying cardiac motion based on Cardiac Magnetic Resonance (CMR) image data.

BACKGROUND

Cardiac problems account for a large portion of modern diseases. Cardiovascular or Cardiac Magnetic Resonance (CMR) is an increasingly important diagnostic tool due to its growing utility in clinical routine. CMR may be considered as a set of magnetic resonance imaging (MRI) techniques designed to assess cardiovascular morphology, ventricular function, myocardial perfusion, tissue characterization and flow quantification. It has become the gold standard for volume quantification, cardiac wall motion assessment, and myocardial scar detection. Since MRI is a non-invasive tool and free of radiation, it is suitable for longitudinal monitoring of treatment effect and follow-up of disease evolution (Tseng et al., 2016).

The main indications for CMR are cardiomyopathies including heart failure, coronary artery disease to assess viability, myocardial stress perfusion, and the anatomical planning of cardiac interventions in congenital patients.

Compared to other techniques, CMR offers excellent spatial resolution and good contrast between tissues. In addition, CMR do not use ionizing radiation and the image quality of images acquired by CMR imaging is not affected by a patient's biotype.

Due to its characteristics, CMR is of great value to assess myocardial wall motion, which typically includes the assessment of the contractile function the left ventricle during the cardiac cycle. This is relevant in several heart diseases but assumes particular interest in ischemic heart disease where asymmetric wall motion abnormalities in the left ventricle are often present. Other diseases may also cause segmental wall motion abnormalities such as myocarditis, hypertrophic cardiomyopathy among others.

The workflow of a CMR study comprises a set of possible sequences and techniques which together provide useful diagnostic and prognostic information. As mentioned, one of the most frequent clinical indications for CMR is ischemic heart disease, one of the leading causes of death worldwide. On this setting, the CMR study is usually composed of, at least, by three studies: cine imaging, perfusion, and late-gadolinium enhancement (LGE).

Here, cine imaging typically provides short movies, which show the heart motion the cardiac cycle, allowing structure, volumes and function evaluation. One of the most important aspects of cine imaging study is the evaluation of myocardial wall motion. This dynamic assessment is performed in multiple anatomical planes that depict the heart in different views (e.g. short axis, 2-chamber long axis, 3-chamber long axis, 4-chamber long axis) in a global and segmental way, in which the motion of 17 segments of the myocardium is usually classified as one of hyperkinetic, normokinetic, hypokinetic, akinetic, dyskinetic, and aneurysmatic. The 17-segment model may be represented as a chart, table, or bipolar map, also referred to as "bulls-eye" plot (Hundley et al. 2009).

Both the perfusion and LGE studies are performed with the use of a contrast agent (e.g. gadolinium). The perfusion images may be acquired during the injection of the contrast agent and under the perfusion of a vasodilator drug that pretends to induce a mismatch of perfusion between areas with normal arteries and areas with obstructed arteries. The myocardial regions supplied by narrowed vessels have a perfusion defect that may be seen as a dark region when compared with healthy myocardium. The LGE study is performed usually 10 minutes after administration of the contrast agent and is the best exam to visualize scarring tissue (which may display as a bright region, due to the delayed washout of the contrast agent from an injured area).

The anatomical segmentation of the heart used in the following description and illustrated and illustrated in FIG. 1A may be described as follows:

FIG. 1A shows a four-chamber sectional view of an exemplary heart 100. A longitudinal axis 120 ("long axis") can be defined as any view that extends substantially parallel to the ventricle septum 122. However, other definitions of this longitudinal axis 120 are possible, for example the electrical heart axis, or an axis extending through the apex 106 of the heart.

The heart can be divided into a plurality of layers, which subsequently extend substantially perpendicular to the longitudinal axis 120. For example, starting from the heart apex 106, the heart can be divided into a bottom layer 130, an apex layer 135, an apical layer 140, a medial layer 150, a basal layer 160, and a top layer 170 (layer not shown). These views of the heart are referred as "short axis".

While this structure is not limiting to the invention, this division has been proven to reduce complexity while still permitting a sufficient spatial resolution of the relevant regions of the heart muscle.

The heart is divided into two ventricles, namely, a left ventricle 102 and a right ventricle 104, which are connected to a left and a right atrium, respectively, such that physiologically, blood flows from the atria to the respective ventricles via a left valve (mitral valve) and a right valve (tricuspid valve). While the left ventricle 102 is responsible for the systemic circulation, the right ventricle 104 is responsible for the pulmonary circulation. The muscle tissue of the left ventricle is thicker than that of the right ventricle and the following description will be based mainly of an assessment of the left ventricle. However, it will be clear to a person skilled in the art that the methods, systems and apparatuses disclosed herein can also be used for assessing the right ventricle.

In order to depict the cardiac motion in a reproducible, standardized way, the muscle tissue of the left ventricle may be illustrated as a "wall motion bulls-eye" 190, as illustrated in FIG. 1C.

FIG. 1B is a drawing for better understanding of the representation of the bulls-eye 190. FIG. 1B depicts sections of a basal layer 160, a medial layer 150, and an apical layer 140 in a view essentially along the longitudinal axis 120.

The views in FIG. 1B show sections through the left ventricular muscle 102 and the right ventricular muscle 104.

Each layer 140, 150, 160 can be further divided into a plurality of segments, namely, each of the circular rings depicting the left ventricle 102 can then be divided into a plurality of segments along a circumferential direction. For example, the basal ring and the medial ring may each be divided in six segments 1-6 and 7-12, respectively, namely, an anterior segment 1, 7, an anteroseptal segment 2, 8, an inferoseptal segment 3, 9, an inferior segment 4, 10, an inferolateral segment 5, 11, and an 5 anterolateral segment 6, 12. The apical ring may be divided into four segments, namely an anterior 13, a septal 14, an inferior 15, and a lateral segment 16, such that the basal 160, medial 150, and apical 140 levels can be divided into a total of 16 segments. Stacking these 16 levels as concentric rings, wherein the basal layer 160 forms the outermost ring 161, the medial layer 150 forms the next ring 151 in a radially inward direction, and the apical layer 140 forms the subsequent next ring 141 in a radially inward direction, and adding a 17th segment 131 in the middle, which represents the anatomical apex of the heart, results in the "wall motion bulls-eye", which allows for depicting the segments of the left ventricular muscle tissue that are segmented both along a direction essentially parallel to the longitudinal heart axis and along a circumferential direction of the ventricle in a standardized 2-dimensional diagram, which is shown in FIG. 1C. This segmentation is routinely used in the clinical field.

FIG. 2 exemplifies a classification for a patient model. In FIG. 2, the bulls-eye diagram is rotated, and segments 1-7 are annotated, which correspond to the segments 1-7 of FIG. 1C. The remaining segments 8-17 have been omitted from FIG. 2, but the spatial relation of the segments is identical to the one depicted in FIG. 2C. In FIG. 2, for example, segments 1, 2, 5, 6, 7, and 8 are classified as class "2", segments 11, 12, 13, 14, 15, 16, and 17 have been classified as class "1", segments 4 and 10 have been classified as class "3", and segments 3 and 9 have been classified as class "4".

For example, the classes (also referred to as movement features below) may correspond to the movement of each segment during the heart cycle. The classes "1" to "4" above can correspond, for example, to the classification: "1": normal, "2": hypokinetic, "3": akinetic, "4": dyskinetic, and "5": aneurysmatic.

While a classification as "normal" implies a physiological contraction movement of the portion of the heart muscle corresponding to a respective segment, a classification as "akinetic" implies an absence of contraction of that segment.

Characterizing heart motion according to the above-described classification system allows for graphically illustrating the heart muscle function in a standardized pattern.

To assess and classify myocardial wall motion for each segment 1-17, the heart action has to be monitored for a certain time period, preferably at least over the course of a complete heart cycle. Additionally, for each point in time, images of the heart are acquired for a plurality of sections along the longitudinal axis of the heart. In other words, for each section across the longitudinal axis of the heart, a time-series of images is acquired, such that a plurality of image sequences for each section are obtained. This method is referred to as "cine imaging" of the heart, as explained above.

More specifically, several images can be acquired along a longitudinal axis over a period of time. As a result, a plurality of subsequent images is acquired that depicts the heart in a series of subsequent cross-sections, which depict the heart muscle, and, particularly, the left ventricle, as annular cross-sections. Each of these images will be referred to in the following as a "slice".

Conventionally, the wall movement of each segment of the wall motion bulls-eye may be evaluated by a human operator, such as a physician, by visually assessing the images obtained by cine imaging.

LIST OF REFERENCES

Tseng et al., Introduction to Cardiovascular Magnetic Resonance: Technical Principles and Clinical Applications, Acta Cardiol Sinica 2016; 32:129-144.

Schulz-Menger et al., Standardized image interpretation and post processing in cardiovascular magnetic resonance: Society for Cardiovascular Magnetic Resonance (SCMR) Board of Trustees Task Force on Standardized Post Processing, Journal of Cardiovascular Magnetic Resonance 2013, 15:35.

Kramer et al., Standardized cardiovascular magnetic resonance (CMR) protocols 2013 update, Journal of Cardiovascular Magnetic Resonance 2013, 15:91.

Hundley et al., Society for Cardiovascular Magnetic Resonance guidelines for reporting cardiovascular magnetic resonance examinations, Journal of Cardiovascular Magnetic Resonance 2009, 11:5.

SUMMARY

In one embodiment, there is provided a method employing a computing device for providing a global cardiac wall motion classification or evaluation for a patient based on Cardiac Magnetic Resonance (CMR) image data acquired from the patient, wherein the CMR image data comprise a plurality of image frames, I(x, y, z, t), acquired for respective two-dimensional slices in at least one longitudinal direction, z, of the patient's heart and for a plurality of times, t, wherein the computing device comprises at least one non-transitory computer readable medium configured to store instructions executable by at least one processor to carry out steps associated with the method, the method comprising a myocardium segmentation step of inputting the plurality of image frames into two or more trained neural networks, applying the trained neural networks in parallel, and fusing an output of each of the trained neural networks into a single output indicating a segmentation, for each of the plurality of image frames, between a first portion indicating muscle tissue of the heart and a second portion indicating surrounding tissue of the heart muscle, and determining a corresponding mask of muscle tissue for the first portion, a slice classification step of assigning each of the plurality of image frames in each slice, z, to an anatomic layer of the heart, and a global classification step using one or more predetermined thresholds and a plurality of the masks and their corresponding anatomic layers to extract therefrom and determine a global classification or evaluation for the patient as having normal wall motion or suspicious or abnormal wall motion.

According to some embodiments, the method may further comprise a movement feature extraction and classification step of, for each of the masks and the corresponding anatomic layers, extracting a movement feature of the heart and classifying the movement feature into one of a number of pre-determined movement features, and an associating step of associating the classified movement feature with the corresponding layer for the cardiac motion classification.

Other embodiments are contemplated, including those described and disclosed herein.

Technical Problem

In conventional methods of classifying the cardiac motion based on CMR cine imaging, visual analysis (e.g. cine evaluation) is highly subjective and requires a long period of time to complete (for example, in the range of 30-60 minutes). Therefore, it is desirable to provide a methodology by which the global and segmental classification of cardiac motion can be provided in a significantly reduced amount of time.

Solution

The various embodiments presented herein address at least some of the above technical problems.

In particular, in view of the limitations discussed above, in accordance with a first embodiment, a computer-implemented method for providing a global and segmental cardiac motion classification based on Cardiac Magnetic Resonance (CMR) image data is provided, wherein the CMR 10 image data comprise a plurality of image frames, I(x, y, z, t), acquired for respective two-dimensional slices in at least one longitudinal direction, z, of the heart and for a plurality of times, t, the method including: a myocardium segmentation step of inputting the plurality of image frames 15 into two or more trained neural networks, applying the trained neural networks in parallel, and fusing an output of each of the trained neural networks into a single output indicating a segmentation, for each of the plurality of image frames, between a first portion indicating muscle tissue of the heart and a second portion indicating surrounding tissue of the heart muscle, and determining a corresponding mask of muscle tissue for the first portion; a slice classification step of assigning each of the plurality of image frames in each slice, z, to an anatomic layer of the heart; a movement feature extraction and classification step of, for each of the masks and the corresponding anatomic layers, extracting a movement feature of the heart and classifying the movement feature into two global classes (e.g., normal vs suspicious), and optionally into one of a number of pre-determined movement features; and optionally an associating step of associating the classified movement feature with the corresponding layer for the cardiac motion classification.

In accordance with a second embodiment, an apparatus for providing a cardiac motion classification based on Cardiac Magnetic Resonance (CMR) image data is disclosed, the apparatus comprising: a processing system including one or more processors; and a memory that stores executable instructions, that, when executed by the processing system, performs operations, the operations executing a computer-implemented method for providing a cardiac motion classification based on Cardiac Magnetic Resonance (CMR) image data, wherein the CMR image data comprise a plurality of image frames, I(x, y, z, t), acquired for respective two-dimensional slices in at least one longitudinal direction, z, of the heart and for a plurality of times, t, the method including: a myocardium segmentation step of inputting the plurality of image frames into two or more trained neural networks, applying the trained neural networks in parallel, and fusing an output of each of the trained neural networks into a single output indicating a segmentation, for each of the plurality of image frames, between a first portion indicating muscle tissue of the heart and a second portion indicating surrounding tissue of the heart muscle, and determining a corresponding mask of muscle tissue for the first portion; a slice classification step of assigning each of the plurality of image frames in each slice, z, to an anatomic layer of the heart; a movement feature extraction and classification step of, for each of the masks and the corresponding anatomic layers, extracting a movement feature of the heart and classifying the movement feature into two global classes (e.g., normal vs suspicious), and optionally into one of a number of pre-determined movement features; and an optional step of associating the classified movement feature with the corresponding layer for the cardiac motion classification.

In accordance with a third embodiment, a computer program is disclosed, which, when executed by a computer, causes the computer to perform the computer-implemented method according to the first example embodiment disclosed herein.

In accordance with a fourth embodiment, a non-transitory computer-readable storage medium storing a computer program is disclosed relating to the third embodiment.

In accordance with a fifth embodiment, there is disclosed a signal carrying a computer program relating to the third embodiment.

Effects

The computer-implemented methods and apparatus described and disclosed herein are implemented to use artificial intelligence (AI) models in classifying cardiac wall motion based on CMR image data, thereby to improve the reliability and reduce the time conventionally needed for the assessment or classification of cardiac wall motion.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the invention will now be explained in detail, by way of non-limiting example only, with reference to the accompanying figures, described below. Like reference numerals appearing in different ones of the figures denote identical or functionally similar elements, unless indicated otherwise.

FIG. 1A shows a four-chamber sectional view of an exemplary heart 100.

FIG. 1B is a drawing for enhancing the understanding of a representation of a bulls-eye.

FIG. 1C depicts a bulls-eye representation.

FIG. 9 illustrates one embodiment of a first dimensionality reduction process.

DETAILED DESCRIPTION

Figure 2:
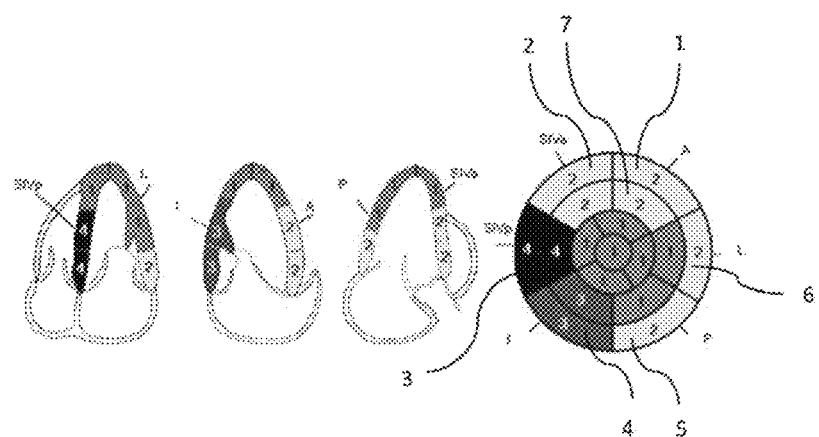
FIG. 2 exemplifies a bulls-eye classification for a patient model and the relation between the bulls-eye and a long axis view.

Example embodiments are now be described in detail with reference to the accompanying drawings.

Where technical features are shown in the drawings, detailed descriptions or any claims are followed by reference signs, the reference signs have been included for the sole purpose of increasing the intelligibility of the drawings, detailed description, and claims. Accordingly, neither the reference signs nor their absence have any limiting effect on the scope of any claim elements.

Figure 3:
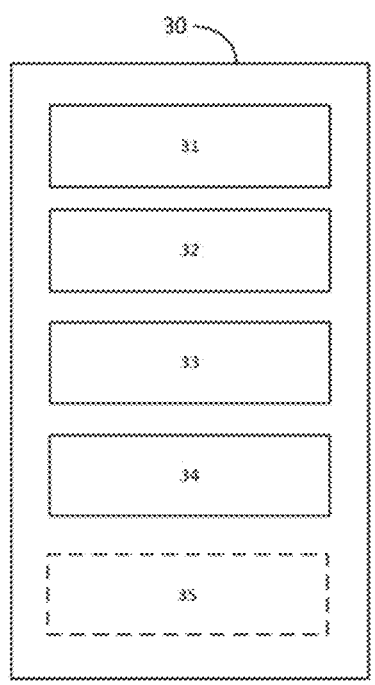
FIG. 3 is a schematic illustration of an apparatus for providing cardiac motion classification based on CMR image data according to one embodiment.

FIG. 3 is a schematic illustration of an apparatus 30 for providing cardiac motion classification based on CMR image data according to an example aspect herein.

In one embodiment, the apparatus comprises a myocardium segmentation module 31, a slice classification module 32, a movement feature extraction and classification module 33, an association module 34 and, optionally, a pre-processing module and/or a post-processing module, referred to here with reference sign 35.

Figure 4:
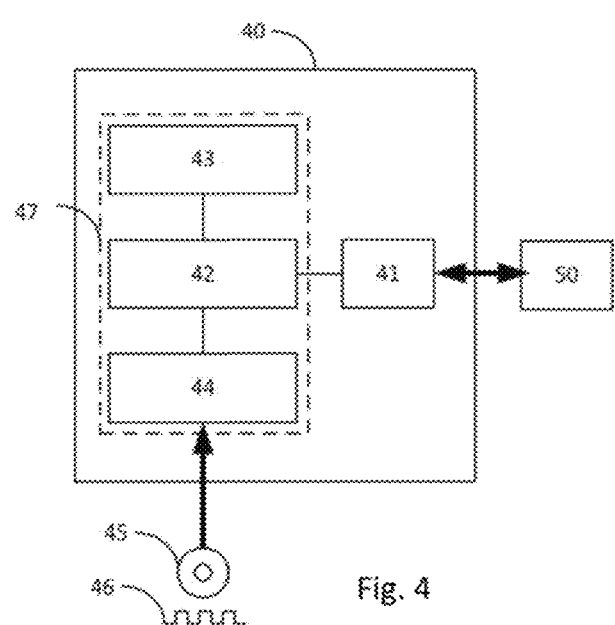
FIG. 4 is a block diagram illustrating an example hardware configuration of the apparatus of FIG. 3, according to one embodiment.

FIG. 4 is a block diagram illustrating an example hardware configuration of the apparatus of FIG. 3 according to one embodiment. In particular, FIG. 4 is a schematic illustration of a programmable signal processing hardware 40, which may, as in the present example embodiment, be configured to function as the apparatus 30 of FIG. 3. The programmable signal processing hardware 40 comprises a communication interface (I/O) 41 for acquiring the CMR image data from an external CMR device or an external CMR database 50.

The signal processing apparatus 40 further comprises one or more processors (e.g. a Central Processing Unit, CPU, or Graphics Processing Unit, GPU) 42, a working memory 43 (e.g., 5 a random access memory) and an instruction store memory or storage unit 44 storing a computer program comprising the computer-readable instructions which, when executed by the processor 42, cause the processor 42 to perform various functions including those of the myocardium segmentation module 31, the slice classification module 32, the movement feature extraction and classification module 33, the association module 34 and, optionally, the pre-processing module and/or the post-processing module 35. The instruction store 44 may comprise a ROM (e.g. in the form of an electrically-erasable programmable read-only memory (EEPROM) or flash memory) which is pre-loaded with the computer-readable instructions. Alternatively, the instruction memory 44 may comprise a RAM or similar type of memory, and the computer-readable instructions of the computer program can be input thereto from a computer program product, such as a non-transitory, computer-readable storage medium 45 in the form of a CD-ROM, DVD-ROM, etc. or a computer-readable signal 46 carrying the computer-readable instructions. In any case, the computer program, when executed by the processor, causes the processor to execute at least one of the methods for providing the cardiac motion classification described herein. It should be noted, however, that the apparatus 30 may alternatively be implemented in non-programmable hardware, such as an application-specific integrated circuit (AS IC).

In one embodiment, a combination 47 of the hardware components shown in FIG. 4, comprising the processor 42, the working memory 43 and the instruction memory 44, is configured to perform functions of the myocardium segmentation module 31, the slice classification module 32, the movement feature extraction and classification module 33, the association module 34 and, optionally, the pre-processing module and/or the post-processing module 35, which functions are described in further detail below.

Figure 5:
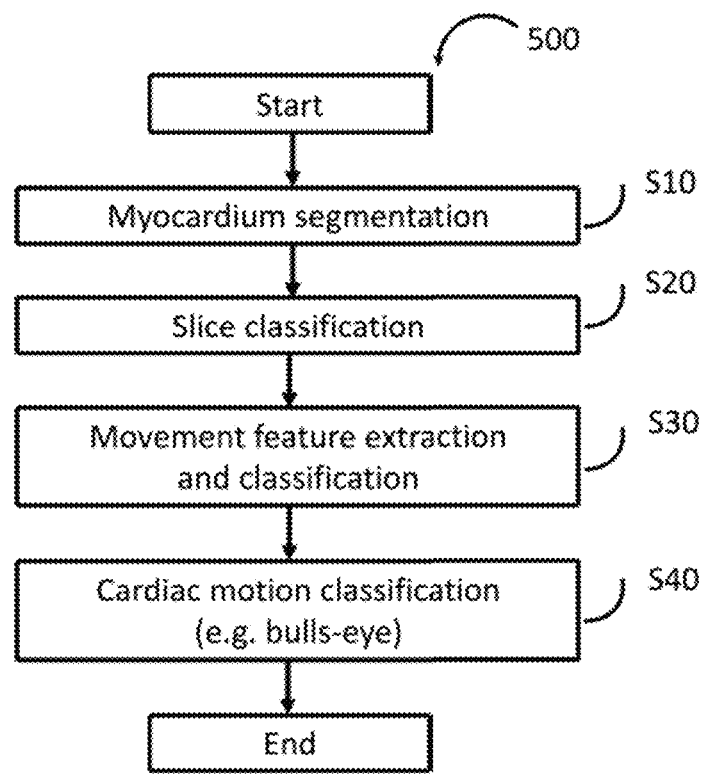
FIG. 5 is a flow diagram illustrating a process by which the apparatus of FIG. 4 may determine global (e.g., normal vs. suspicious) or segmental cardiac motion classification according to one embodiment.

FIG. 5 is a flow diagram illustrating one embodiment of a method or process 500 by which the apparatus 30 of FIG. 3 may determine global (e.g., normal vs. suspicious or abnormal) or segmental cardiac motion classification.

The method of FIG. 5 is based on patient CMR image data, which may be acquired during a CMR image scan in a medical facility. Here, the CMR image data may also include patient-specific data (such as height, weight, age, gender) which may also be used for the determination of the global (e.g., normal vs. suspicious or abnormal) or segmental cardiac motion classification, as is further described below. FIG. 5, however, illustrates an embodiment where segmental cardiac motion classification is carried out in steps S10 through S40, which comprise myocardium segmentation (step S10), slice classification (step S20), movement feature classification (step S30), and cardiac motion classification (step S40), further details of which are discussed below.

In an alternative to the segmental cardiac motion classification method embodiment illustrated in FIG. 5, in another embodiment global cardiac motion evaluation is carried out, which according to one embodiment comprises steps S10, S20 and S30 of FIG. 5, but where step S40 is replaced with a single cardiac wall motion classification or evaluation step S50 (not shown in FIG. 5), which comprises a global analysis of the data and results provided in preceding steps S10, S20, and S30, the output of which in one embodiment is the patient either has "normal" cardiac wall motion, or the patient has "suspicious" or "abnormal" cardiac wall motion. In other embodiments, the output of step S50 is one or more of a measure or degree of the "normalness" and/or "abnormality" of the patient's cardiac wall motion.

In a typical clinical setting, it has been discovered that approximately 70% of all patients who are evaluated for cardiac wall motion abnormalities have normal cardiac wall motion, and whose cardiac condition therefore likely does not merit further investigative effort or expense. The remaining approximately 30% of patients who are evaluated for cardiac wall motion abnormalities do, however, have suspicious or abnormal cardiac wall motion that does indeed merit further investigation or expense. The various embodiments of the global cardiac wall motion evaluation methods described and disclosed herein permit physicians to determine, on an initial and threshold basis, quickly, efficiently, and at relatively low cost, which patients should be subjected to additional more exhaustive and detailed cardiac wall motion or other tests and procedures, and which patients do not require such additional tests and procedures. Collectively, therefore, results provided by the global cardiac wall motion evaluation methods described and disclosed herein permit cardiologists to focus their time and effort on those cardiac patients who require further diagnostic and therapeutic attention, resulting in more efficient delivery of medical care, and substantially reduced medical care costs.

According to one embodiment, global evaluation or classification method comprises applying at least one or a plurality of pre-trained neural networks to each output of the dimensionality reduction step outputs to extract different features. Those features are then concatenated with relevant patient specific data, and are fed to a machine learning classifier which outputs a probability of the patient having "normal" vs. "suspicious" or "abnormal" cardiac wall motion. In one embodiment, a threshold for the probabilities associated with "normal" vs. "suspicious" cardiac wall motion may be defined or determined by studying the probabilities associated with different annotated patient populations. The threshold is a configuration parameter which can be tweaked by the physician or health care provider during actual use as a calibration step.

Given the probability, if it is higher than the threshold, the patient is deemed as "suspicious" or "abnormal" as regards cardiac wall motion, and is deemed as "normal" if the probability is less than the threshold". As discussed above, however, other global classification or evaluation embodiments are contemplated for this step, such as the output of step S50 being one or more of a measure or degree of the "normalness" and/or "abnormality of the patient's cardiac wall motion.

In one embodiment, patient CMR data includes 4-dimensional (4D) data: Each image frame depicts a two-dimensional section of the heart in a plane (x,y plane) that may be substantially perpendicular to the longitudinal axis 120. A plurality of such image frames, which are taken on different times are referred to as a slice, and a plurality of such slices are referred to as the 4D stack of image frames. Acquiring such a stack of image frames allows for depicting the movement of the heart over time.

Figure 6:
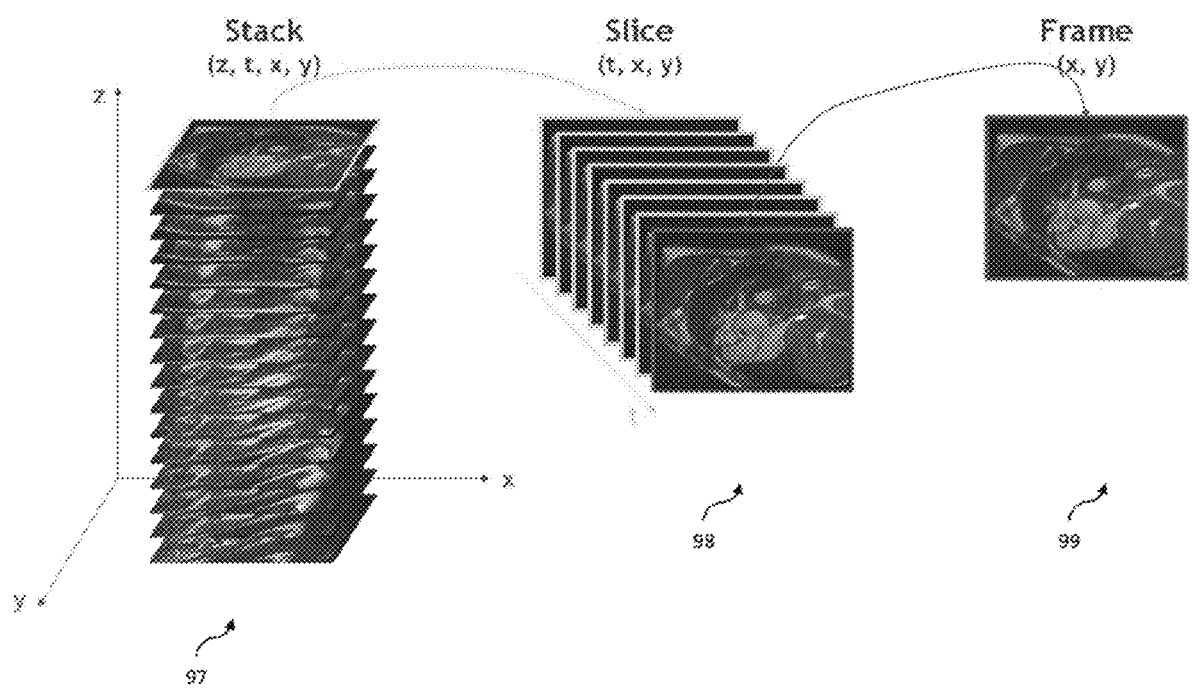
FIG. 6 illustrates CMR image data in a stack, a slice and an image frame.

More specifically, as illustrated in FIG. 6, in one embodiment the CMR image data may comprise a plurality of image frames I(x, y, z, t) acquired for respective two-dimensional slices in at least one longitudinal direction z of the heart and for a plurality of times t. Here, the direction z may be along the so-called short-axis (SA) direction or the long-axis (LA) direction, and the two-dimensional image frames may indicate a grayscale intensity value I, as measured by the CMR image scan.

More specifically, FIG. 6 illustrates the general concept of one embodiment of the image data used herein. As shown in FIG. 6, an image frame 99 is an image at a given point in time (T=t), at a given position at the longitudinal axis 120 (z-axis) (Z=z). A slice 98 is a plurality of (or all) image frames at a given position along the z-axis (Z=z, t). A stack 97 is a plurality of (or all) slices over time (z, t), i.e. the 4D CMR image data.

In process step S10 of FIG. 5, the myocardium segmentation module 31 inputs the plurality of image frames into two or more trained neural networks (also referred to as AI models below), subsequently applies the trained neural networks in parallel on the inputted image frames, and fuses, for each of the inputted image frame, an output of each of the trained neural networks into a single output. The single output indicates or predicts a segmentation, for each of the plurality of image frames, between a first portion indicating muscle tissue of the heart and a second portion indicating surrounding tissue of the heart muscle. Using this segmentation, a corresponding mask of muscle tissue for the first portion in each of the image frames is determined. According to one embodiment, this mask identifies the myocardium in the image frame.

Figure 7:
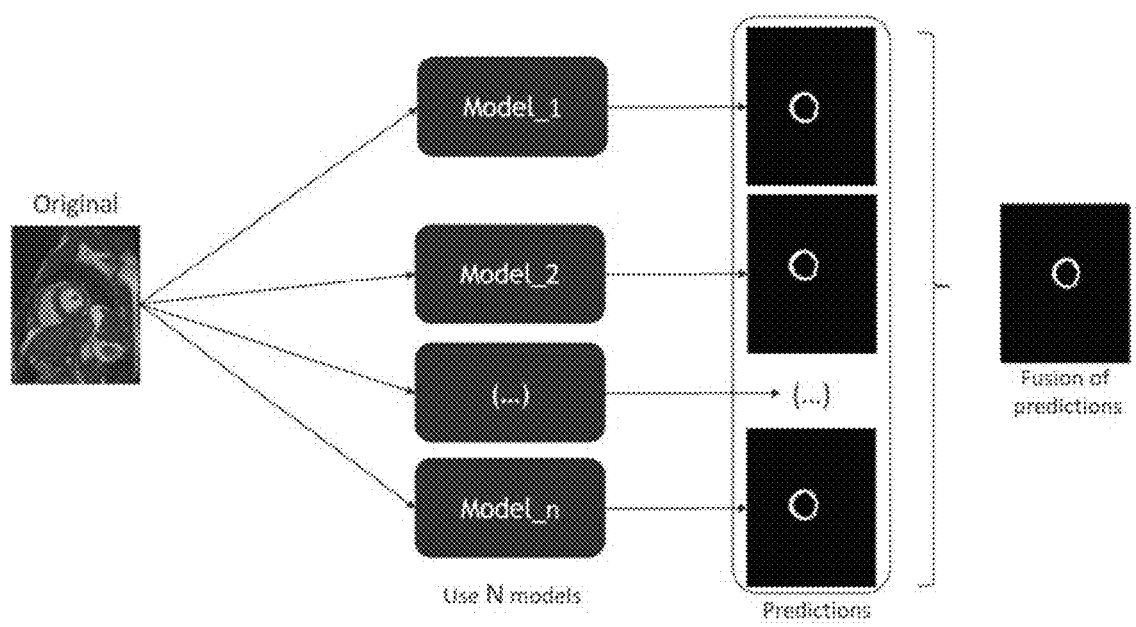
FIG. 7 illustrates one embodiment of myocardium segmentation.

As further illustrated in FIG. 7, an original image frame or a set of image frames is inputted into a plurality of AI models (trained neural networks), referred to in FIG. 7 as Model 1, Model_2, . . . Model n, indicating that n trained neural networks are applied in parallel for the original image frame. Each trained neural network predicts or determines a portion in the image frame corresponding to muscle tissue (bright ring shape in FIG. 7) and a portion in the image frame corresponding to non-myocardium tissue, i.e. the tissue or body liquid surrounding the muscle tissue (the dark area in FIG. 7). As such, each trained neural network predicts a segmentation between a first portion that indicates muscle tissue and a second portion that indicates surrounding tissue.

As illustrated in FIG. 7, the outputs of the parallel predictions of the trained neural network are fused to determine a single output. One skilled in the art will now understand and appreciate that there may be various ways to perform such a fusion, for example based on an averaging procedure, a statistical averaging procedure, for example applying different weights to the respective n trained neural networks, by using different combinatorial or statistical methods in dependence on the layer position of the heart, i.e. applying such methods in dependence of whether the image frame is for the basal layer or the apical layer, or other suitable methods or techniques.

Based on the fused output, a corresponding mask of muscle tissue is determined, i.e., a binary data structure distinguishing between muscle tissue and non-muscle tissue. In FIG. 7, the mask is shown as a bright ring-like shape in the fused output image.

In connection with determination of the masks, a correction process may be implemented for false positive and false negative mask parts, that is, parts that ought to belong to the myocardium mask, but have not been determined as belonging to the mask, and false positive mask parts, that is, parts that should not be comprised in the mask, but have been determined as belonging to the mask. In particular, this may comprise a step of removing false positive blobs, that is, a step of removing small objects not connected to the left ventricle, using a 4D-connection. Further, the step may comprise a ROI (Region of interest) filtering step in which the most probable region of the ventricle is determined and in which then objects that do not intercept with the ROI are filtered out.

In addition, the mask determination step may comprise a mask reconstruction step, which comprises a hole filling and mask smoothing step in which "holes" in the mask, that is, small portions on the image that have not been detected as belonging to the mask are added to the mask region. In addition, a half-moon shape correction may be used for the image frames depicting the basal portion, and a ring shape correction for the medial and apical portions.

Here, the trained neural networks applied in parallel on each of the original image frames, as illustrated in FIG. 7, may comprise two or more of:

a first neural network (also referred to as a 2D network below) which considers the plurality of image frames, I(x, y, z, t) individually as inputs (i.e., the 2D image frames in one respective slice z and at one respective time t);

a second neural network (also referred to as a 2Dt network below) which considers, for each of the plurality of image frames, I(x, y, z, t), also a previous time image frame, I(x, y, z, t−1), and a subsequent time image frame, I(x, y, z, t+1), as inputs (i.e., the 2D image frames in one respective slice z and at three respective times t−1, t, t+1);

a third neural network (also referred to as a 2Dz network below) which considers, for each of the plurality of image frames, I (x, y, z, t), also a previous slice image frame, I(x, y, z−1, t), and a subsequent slice image frame, I(x, y, z+1, t), as inputs (i.e., the 2D image frames in three respective slices z−1, z, z+1 and at one respective time t);

a fourth neural network (also referred to as a 3DT network below) which considers all of the plurality of image frames, I(x, y, z, t=1 . . . N) for a given slice (i.e., the 2D image frames in one respective slices z and at all respective times t=1 . . . N of the slice z); and a fifth neural network (also referred to as a 2DZ network below) which considers all of the plurality of image frames, I(x, y, z=1 . . . M, t) for a given time (i.e., the 2D image frames in all respective slices z=1 . . . M and at one respective time t).

One skilled in the art will now appreciate and understand that the foregoing examples of neural networks may be applied to image data and provided for a stack of image data which has a plurality of slices z=1 . . . M. which is provided for a plurality of times t=1 . . . N.

One skilled in the art will now further appreciate and understand that the output of the above first, second, and third neural networks is a single binary mask (as described above, showing the position of the myocardium) while the outputs of the above fourth and fifth neural network have the same 3D output in the time direction (t=1 . . . N) or in the slice direction (z=1 . . . M), but that the mask(s) may individually be determined using the 3D output.

On the other hand, if image data are available only for a single slice z but for a plurality of times, then the trained neural networks which are applied in parallel on each of the original image frames may comprise two or more of:

a first neural network (also referred to as a 2D network below) which considers the plurality of image frames, I (x, y, z, t), individually as input (i.e., the 2D image frames in one respective slice z and at one respective time t);

a second neural network (also referred to as a 2Dt network below) which considers, for each of the plurality of image frames, I(x, y, z, t), also a previous time image frame, I(x, y, z, t−1) (i.e., the 2D image frames in one respective slice z and at three respective times t−1, t, t+1), and a subsequent time image frame, I(x, y, z, t+1), as an input; and a third neural network (also referred to as 3DT network below), which considers all of the plurality of image frames, I(x, y, z, t=1 . . . N) for a given slice (i.e., the 2D image frames in one respective slice z and at all respective times t=1 . . . N of the slice z).

In process step S20 of FIG. 5, and according to one embodiment, the slice classification module 32 assigns each of the plurality of image frames in each slice z to an anatomic layer of the heart. This may be performed on the basis of the original image frames, for example, in parallel with the myocardium segmentation.

Here, the slice classification preferably assigns each image frame to one anatomic layer of the heart. The anatomic layer may be selected from a group consisting of: top, a basal layer, a medial layer, an apical layer, bottom, as explained above.

For this, the input data are preferably normalized patient CMR data, for example using clinical or patient-specific data (such as height, weight, age, gender), as will be further explained below. In an assigning procedure, each layer of the heart, such as a bottom layer 130, an apical layer 140, a medial layer 150, and a basal layer 160, and a top layer 170 can each be depicted in a plurality of image frames. In one embodiment, the slice classification step assigns each image frame to at most one layer: for example, a plurality of image frames depicting the apical portion of the heart may be assigned to the apical layer 140, a plurality of image frames depicting the medial portion of the heart may be assigned to the medial layer 150, and so forth. Note that each image frame is assigned to at most one of these layers 130, 140, 150, 160, and 170. This assigning step can also be referred to as a "labelling step", in which image frames are labelled with regard to the layer which they are assigned to.

In process step S30 of FIG. 5, and according to one embodiment, the movement feature and classification module 33 extracts, for each of the determined masks and the corresponding anatomic layers, a movement feature of the heart and classifies the extracted movement feature into two global classes (normal vs. suspicious) and optionally into one of a number of pre-determined movement features.

Here, the motion tracking may thus be considered as tracking the myocardium walls' motion (global or segmental) from its deformation in time and the pre-determined movement features may be hyperkinetic motion, normokinetic motion, hypokinetic motion, akinetic motion, dyskinetic motion, aneurismatic motion, tardykinetic motion, and paradoxical motion and the movement feature and classification module 33 may use a trained neural network to classify the extracted movement feature into two global classes (normal vs. suspicious) and optionally into one of a number of pre-determined movement features.

Here, the movement feature and classification module 33, in segmental classification embodiments, may divide the mask into respective segments, for example 4 or 6 segments, and may classify the extracted movement features for each of the segments of the corresponding layer. In some embodiments, the above masks (defining a ring-like shape in a corresponding anatomic layer of the heart) may be divided into a number of individual segments, for example 4 or 6 segments.

For example, two ventricular insertions may be identified for each image frame. The two ventricular insertion points correspond to the coordinates where the myocardium walls from both ventricles intersect. The two ventricular insertions points are thus positioned in the vicinity of the separation between the anterior and the anteroseptal, and between the inferior and inferoseptal segments, and only on the basal and medial layers. The ventricular insertions identify the coordinates of insertion points in each frame where the segments within a layer are separated from each other. For example, within the basal ring, the anterior segment and the anteroseptal segment separated by an insertion point, and so forth. The ventricular insertions can, for example, be performed by determining the center of the mask and then dividing the myocardium mask into six equiangular segments around the center for the basal 160 and medial 150 layer and dividing the myocardium mask into a number of equiangular segments around the center for the apical layer 140. On the apical layer, the middle point between the two insertions is again taken as reference. From there, the separation between the septal and anterior segments is obtained by clockwise rotation of 45° and the separation between the septal and inferior is obtained by counter-clockwise rotation of 45°. The other 2 separations are equiangularly defined from the previous (so each segment corresponds to 90°).

Here, a trained neural network may predict the two ventricular insertion points on a first image frame of a slice or alternatively on all image frames. Then, deformation fields are considered by the trained neural network. These deformation fields are defined as mappings indicating a direction and/or a magnitude of how much each pixel in every image frame moves over time. By thus following or predicting the positions of the two ventricular insertion points along the image frames in time, the movement feature and classification module 33 (in a segmental classification embodiment) may divide the mask into the respective segments.

Based on the above deformation fields, the movement feature and classification module 33 may compute one or more time series with regard to the mask characteristics. In particular, for different regions of the mask and for at least a pre-determined number of image frames in time, for example a portion or all image frames in a particular slice, a time series of a tracked deformation feature may be considered with regard to one or more of an inner radius of the mask, an outer radius of the mask, an inner curvature of the mask, an outer curvature of the mask, a bloodpool area, and a segment thickness.

In other words, based on the above deformation fields, the time series tracks a temporal behaviour of a movement feature (e.g., inner radius of the mask, outer radius of the mask, inner curvature of the mask, outer curvature of the mask, bloodpool area, a segment thickness) and extracts this temporal behaviour as the movement feature. This indicates, for example, the amount of movement of a particular segment in a particular anatomic layer of the heart.

The movement feature extraction and classification module may then input the computed time series of the tracked deformation feature into a trained neural network to classify the extracted movement feature into two global classes (normal vs. suspicious), and optionally into one of a number of pre-determined movement features.

Alternatively, statistical values extracted from a statistical analysis of the extracted time series such as an average, a standard deviation, a kurtosis, a skewness, and the like, may be input into a trained neural network to classify the extracted movement feature into two global classes (normal vs. suspicious), and optionally into one of a number of pre-determined movement features.

Figure 8:
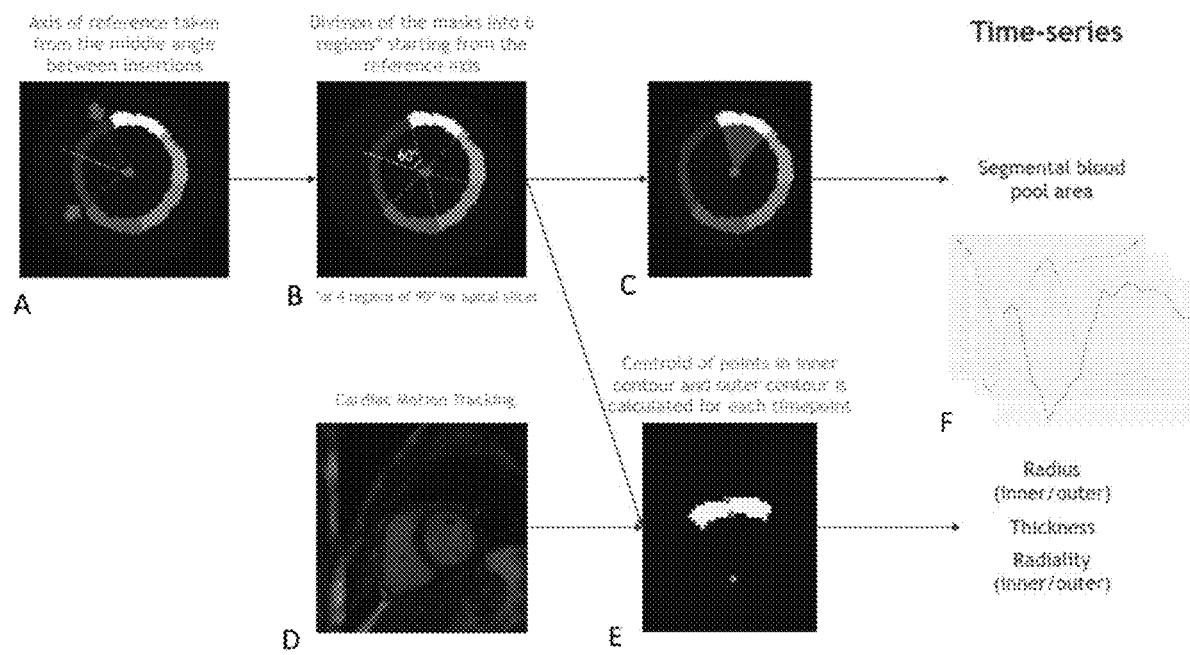
FIG. 8 illustrates one embodiment of the movement feature extraction.

The above embodiments of illustrating movement feature extraction are further shown in FIG. 8. Here, the two ventricular insertions are indicated as arrows in section A of FIG. 8. In one embodiment, an axis of reference may be taken from a middle angle between the two ventricular insertions. According to section B of FIG. 8, a division of the mask into 6 segments (regions of 60°) or 4 segments (regions of 90°) may be performed starting from the thus defined reference axis. Further, according to section C of FIG. 8, a segmented blood pool area may be considered with regard to each segment, whereby the segmented blood pool area is defined by a circular slice section area for the respective segments. Based on cardiac motion tracking according to sections D and E of FIG. 8, a trained neural network may predict a deformation direction and/or deformation magnitude that occurs between a given image frame and a consecutive image frame in time. Based thereon, for example, a centroid of points in an inner contour and an outer contour may be calculated for each timepoint, so that a corresponding time-series may be calculated for one or more of the inner radius of the mask, the outer radius of the mask, the inner curvature of the mask, the outer curvature of the mask, the blood pool area, and the segment thickness.

These extracted time-series are a measure of the direction and magnitude of the myocardium motion for the respective segments, and may be subsequently used for movement classification (global or segmental), which may be complemented by a statistical analysis on the extracted time-series.

The movement feature extraction and classification module may further apply a dimensionality reduction process. In some embodiments, this dimensionality reduction process results in data compression.

According to a first example of the dimensionality reduction process, as illustrated in FIG. 9, a dimensionality reduction step may start by determining an inner radius and/or an outer radius of the mask over all angles θ of the mask from 0° to 360°. Preferably, the angle information (from 0° to 360°) is calculated by taking into account and following the ventricular insertion positions, as explained above. For example, the angle of 0° may be defined by a line that passes through the centroid of the bloodpool area (corresponding to the center of the inner contour of the mask) and the middle point between the two ventricular insertion points. Based on such a polar coordinates representation, the mask information may be reduced to a couple of (r, θ) lines.

Based thereon, each image frame may thus be reduced into a first data representation defining the inner radius and/or the outer radius of the mask over the angle θ, and thus reducing a 4D image data representation of the image frame I(x, y, z, t) (as described above) into a first 3D data representation of an image frame I(θ, z, t) in which a first image intensity now represents a radius value of the inner radius and/or the outer radius. This first 3D data representation is illustrated in FIG. 10, indicating for respective angles θ, for respective times t (or correspondingly the frame number), and the number of slices z that the intensity gray value defines a corresponding radius value.

Figure 10:
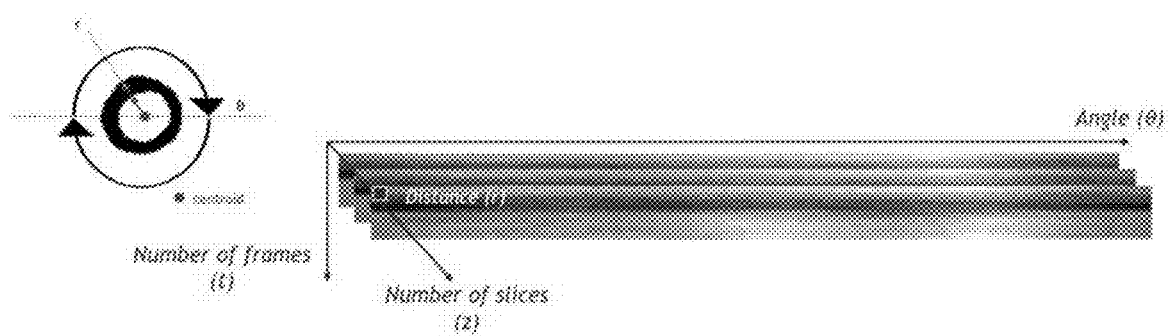
FIG. 10 illustrates further aspects of the first dimensionality reduction process.
Figure 11:
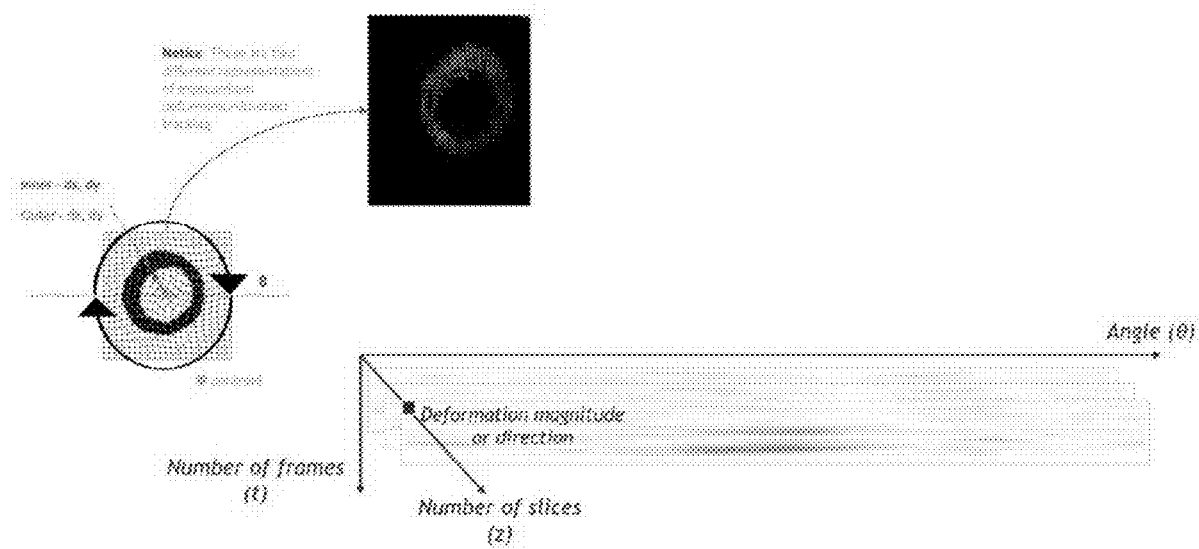
FIG. 11 illustrates one embodiment of a second dimensionality reduction process.

The dimensionality reduction steps described and disclosed herein, such as those illustrated in FIGS. 9, 10 and 11 hereof, permit distance to center and deformation of the myocardium segmentation contours (inner and outer) ranging between 0 to and 360° to be sampled or measured.

With that being said, and according to some embodiments, the total dimensionality of the data can be reduced from 4 (x, y, z, t) to 3 (θ, z, t) which significantly decreases the number of data points, and therefore reduces the computational horsepower required to provide useful results in a timely manner. That is, With fewer data points to be analyzed, the required computational power decreases significantly.

Then, using the reduced first 3D data representation, a cardiac motion classifying step may use a trained neural network to directly classify an extracted movement feature into one of the number of pre-determined movement features based on the first image intensity (representing radius information of the mask).

According to a second embodiment of a dimensionality reduction process, a dimensionality reduction step may start by determining a deformation direction and/or a deformation magnitude with regard to the mask over all angles 8 of the mask from 0° to 360°. According to some embodiment, the deformation direction and/or a deformation magnitude may be determined by considering infinitesimal voxel deformations dx and dy related to the movement of structures present between successive frames in time. Then each image frame may be reduced into a second representation defining the deformation direction and/or the deformation magnitude of the mask over the angle θ, and thus reducing the 4D image data representation of the image frame, I(x, y, z, t), into a second 3D data representation of the image frame, I(θ, z, t) in which a second image intensity now represents the deformation direction and/or the deformation magnitude (of a frame-to-frame motion). This second 3D data representation is illustrated in FIG. 11, indicating for respective angles θ, for respective times t (or correspondingly the frame number), and the number of slices z that the intensity gray value defines a corresponding deformation magnitude or deformation direction. As indicated in FIG. 11, the deformation magnitude or deformation direction indicated based on the infinitesimal voxel deformations dx and dy with regard to the movement of structures present between successive frames in time are different representations with regard to myocardium deformation and motion tracking as compared to the deformation fields defined as mappings indicating a direction and/or a magnitude of how much each pixel in every image frame moves over time. Then, using the reduced second 3D data representation, a cardiac motion classifying step may use a trained neural network to directly classify an extracted movement feature into two global classes (normal vs. suspicious), and optionally into one of a number of pre-determined movement features based on the image intensity.

In process step S40 of FIG. 5, and in a segmental classification embodiment the association module 34 associates the classified movement feature with the corresponding layer for the cardiac motion classification. This association may be considered as a general data structure such as a table, a chart, a map, or the like that defines the movement feature(s) for each heart layer.

When the movement features are further classified with regard to individual segments in a layer of the heart (as described above), then the association module 34 may associate the classified movement features with the corresponding segments of the layer for the cardiac motion classification. In one embodiment, this association is the bulls-eye segmental cardiac motion classification, as explained above.

According to a further embodiment, the apparatus may be configured with a pre-processing module (generally referred to with reference sign 35 in FIG. 3). The pre-processing module is configured to perform a pre-processing step on the plurality of image frames by which the image data are made more uniform.

This uniformization or normalization of the image data in the image frames may be achieved in a plurality of ways, which may be performed individually or in combination. For example, a unifying step may be implemented to unify CMR image data to a same target resolution and/or to a same target dimension.

Alternatively, or in combination, a unifying step may be implemented to provide a more uniform (intensity) grayscale characteristics, for example, so that the grayscale of the image frames have a common mean value and a common standard variation.

Alternatively, or in combination, the pre-processing module may further align corresponding features of adjacent (in the slice direction) image frames with one another. Different alignment strategies may be implemented. For example, assuming a long-axis 4-chamber and a 2-chamber view are aligned with each other. Then, for each short-axis slice in the stack, rigid translations may be applied to maximize the overlap between the long-axis and short-axis plane. As such, a misalignment between respective image frames may be reduced which may arise from the CMR image acquisition process, for example during breathing of a patient. This reduces artifacts, for example movement artifacts which result from the fact that the heart moves during the imaging process, for example due to the heart motion and due to movements during the breath cycle. Reducing the influence of these artifacts may thus provide more accurate cardiac motion classification.

The above uniformization or normalization of the image data may additionally be performed on an intra-patient or inter-patient level, i.e., by taking only the patient's information into account or by taking into account the information of a sample population (multiple patient).

According to a further embodiment, the apparatus may be configured with a post-processing module (generally referred to with reference sign 35 in FIG. 3). The post-processing module is preferably a module for providing error correction and ensuring classification accuracy.

Figure 12:
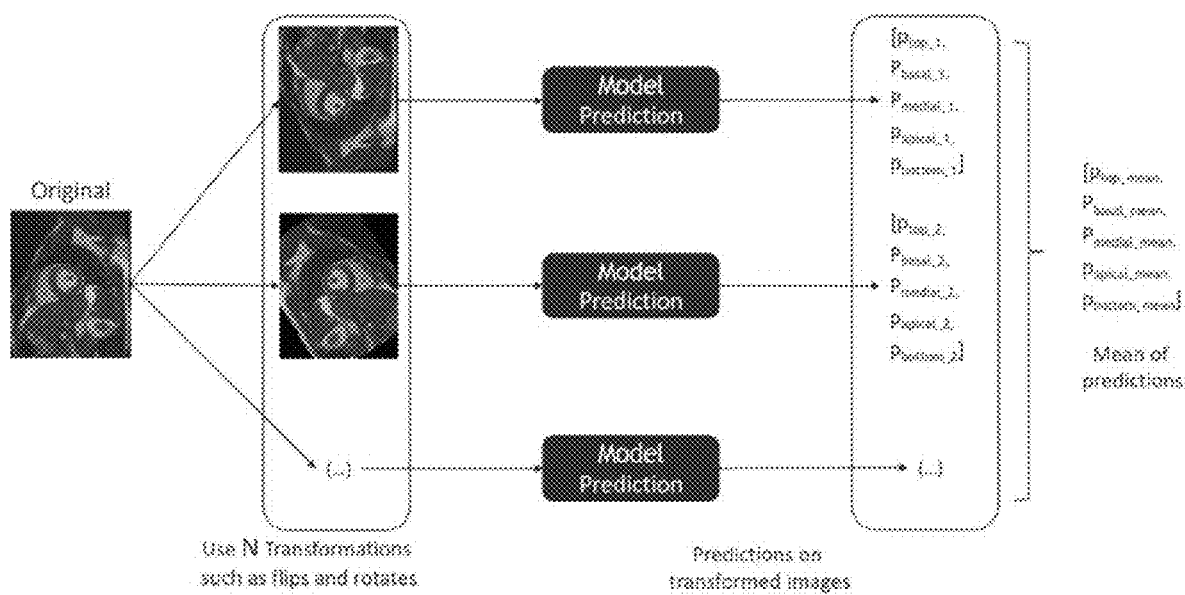
FIG. 12 illustrates a of post-processing to assign layer probabilities.

For example, the post-processing module 35 may be configured to determine a layer probability, p, indicating a probability value that the inputted image frame belongs to an anatomic layer of the heart. The skilled person understands that this may be achieved in a plurality of ways. For example, a pre-determined number of transformed image frames may be generated from an image frame. Such a transformation may be implemented, for example, by rotating the image frame, by mirroring the image frame (image flip), scaling the image frame, or the like. Subsequently, the original image frame and the transformed image frames may be inputted into a trained neural network to determine the layer probability, as illustrated in FIG. 12. The trained neural network(s) may generate probability values p top, p_basal, p_medial, p apical, p_bottom for each input image i= 1, ..., N, so that the final result may be determined as a mean value of the probability values.

The post-processing module may further incorporate spatial and/or temporal coherence of output predictions of the at least one deep neural network. While the input image frames are naturally ordered by the CMR data acquisition process, this guarantees that the predicted anatomical layer classes (output by the one or more neural networks) are ordered correctly (in time and space). Here, empirical rules may be followed, for instance, the number of classes for a given slice, over time, should be 1 (always the same) or 2. For the second case it is also known that the number of temporal transitions between classes should not be higher than 2.

Figure 13:
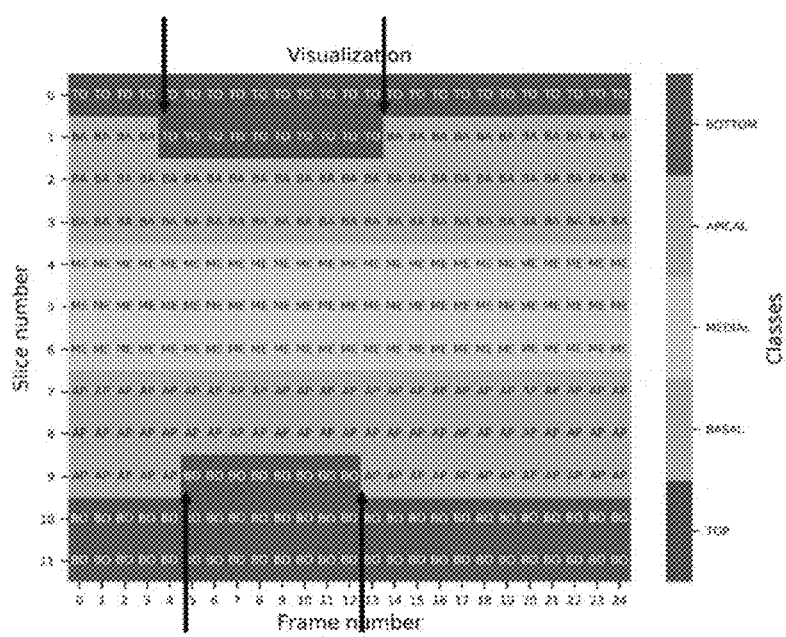
FIG. 13 illustrates a of post-processing to correct misclassification of slices.

For example, as shown in FIG. 13, this post-processing step may identify outputs that are misclassified, in slice number 2, as belonging to the top layer (instead of the appropriate basal layer) or are misclassified, in slice number 8, as belonging to the bottom layer (instead of the appropriate apical layer). The post-processing module 35 may thus act over the trained neural network's predictions, so that possible misclassifications or misassignments can be corrected. For a given frame the post-processing module thus considers the predictions made and infers if that given prediction is appropriate or anomalous attending to the prediction made to the adjacent (in time and space) frames.

By applying this post-processing step, "outliers", that is, individual misassigned image frames, may be removed or re-assigned accordingly.

Figure 14:
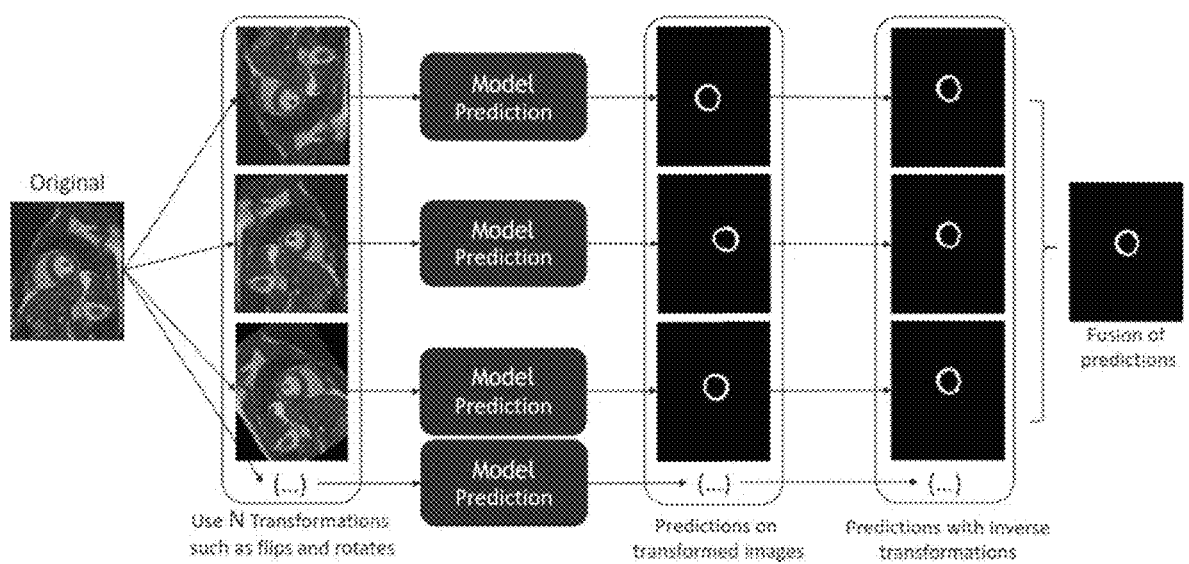
FIG. 14 illustrates one embodiment of post-processing.

The post-processing module may further create a plurality of versions of an image frame of the plurality of image frames and apply the plurality of versions to at least one (deep) neural network. This post-processing step is illustrated in FIG. 14. Here, the plurality of versions of the image frame may be created by transforming or deforming the image frame, for example by rotating the image frame, mirroring (flip) the image frame, and/or scaling the image frame. Then, to the output of the neural network, an inverted transformation is also applied so that all outputs are comparable in terms of pixel to pixel representation. Then, the output of the at least one (deep) neural network with regard to the inputted plurality of versions of the image frame may be fused, for example by applying an averaging procedure or another statistical procedure on the predicted outputs, in order to reinforce the at least one (deep) neural network and to make it more reliable and robust.

In addition, the post-processing module step may select a suitable combination of trained neural networks, for example based on the output of the 2D, 2Dt, 3Dt, 3DT, 3DZ neural networks described above. This allows for selecting the best models and to use them together to achieve a new model with better results as compared to each model used individually.

According to some embodiments, each of the myocardium segmentation module and/or the slice classification module and/or the movement feature extraction module and classification module and/or the association module may further use patient data, preferably as a direct input into corresponding trained neural networks or as a normalization component. Patient data may indicate patient height, weight, age, gender, or any other specific patient data that may be indicative of individual cardiac motion. Preferably, this may be used to normalize the extracted movement feature to the individual patient.

According to some embodiments, each of the myocardium segmentation module and/or slice classification module and/or the movement feature extraction module and classification module and/or the association module may use one or more trained neural networks, preferably one or more deep neural networks. In some embodiments, trained neural networks parametrize a mathematical model such that the parameters incorporate information on patterns of the inputted data. To do so, the neural networks may be fed with known inputs, and the output error in relation to the desired output may be measured. This error is then used to update the model parameters until the errors are minimized. This process of feeding the data to the neural network model, to measure the error and to update its parameters is commonly known as "training" a neural network model. For example, a convolutional neural network may be trained using known input data, such as pre-existing data with pre-existing assignments, so as to train the network to detect image patterns that allow, for example, a classifying of each frame as belonging to one of the layers as described above, or a classification of a movement feature as described above.

Examples of trained neural networks include, but are not limited to, a feed forward network, recurrent neural network, neural network with external memory, and a network with attention mechanisms. An exemplary code to be used for the trained neural network may be derived from tensorflow libraries.

We claim:

1. A method employing a computing device for providing a global cardiac wall motion classification or evaluation for a patient based on Cardiac Magnetic Resonance (CMR) image data acquired from the patient, wherein the CMR image data comprise a plurality of image frames, $I(x, y, z, t)$, acquired for respective two-dimensional slices in at least one longitudinal direction, $z$, of the patient's heart and for a plurality of times, $t$, wherein the computing device comprises at least one non-transitory computer readable medium configured to store instructions executable by at least one processor to carry out steps associated with the method, the method comprising:
   a myocardium segmentation step of inputting the plurality of image frames into two or more trained neural networks, applying the trained neural networks in parallel, and fusing an output of each of the trained neural networks into a single output indicating a segmentation, for each of the plurality of image frames, between a first portion indicating muscle tissue of the heart and a second portion indicating surrounding tissue of the heart muscle, and determining a corresponding mask of muscle tissue for the first portion;
   a slice classification step of assigning each of the plurality of image frames in each slice, $z$, to an anatomic layer of the heart;
   a movement feature extraction step of, for each of the masks and the corresponding anatomic layers, extracting a movement feature of the heart and classifying the movement feature into one of a number of pre-determined movement features, and
   a global classification step using one or more predetermined thresholds and a plurality of the masks and their corresponding anatomic layers to extract therefrom and determine a global classification or evaluation for the patient as having normal wall motion or suspicious or abnormal wall motion.

2. The method of claim 1, further comprising an associating step of associating the classified movement feature with the corresponding layer for the cardiac motion classification.

3. The method of claim 2, wherein the pre-determined movement features comprises hyperkinetic motion, normokinetic motion, hypokinetic motion, akinetic motion, dyskinetic motion, aneurysmatic motion, tardykinetic motion, and paradoxical motion.

4. The method of claim 1, further comprising a pre-processing step applied to the plurality of image frames, the pre-processing step comprising one or more of:
   a unifying step of unifying the CMR image data to one of a same target resolution, same target dimensions, and uniformization of a grayscale characteristics, and
   a slice alignment step of aligning corresponding features of adjacent image frames with each other.

5. The method of claim 1, wherein the trained neural networks comprise two or more of:
   a first neural network which considers the plurality of image frames, $I(x, y, z, t)$, individually as inputs thereto;
   a second neural network which considers, for each of the plurality of image frames, $I(x, y, z, t)$, also a previous time image frame, $I(x, y, z, t-1)$, and a subsequent time image frame, $I(x, y, z, t+1)$, as inputs thereto;
   a third neural network which considers, for each of the plurality of image frames, $I(x, y, z, t)$, also a previous slice image frame, $I(x, y, z-1, t)$, and a subsequent slice image frame, $I(x, y, z+1, t)$, as inputs thereto;
   a fourth neural network which considers all of the plurality of image frames, $I(x, y, z, t=1 \ldots N)$ for a given slice; and
   a fifth neural network which considers all of the plurality of image frames, $I(x, y, z=1 \ldots M, t)$ for a given time.

6. The method of claim 1, wherein the slice classification step further assigns each image frame to one anatomic layer selected from a group consisting of: top, a basal layer, a medial layer, an apical layer, bottom.

7. The method of claim 1, wherein a pre-determined number of transformed image frames are generated from an image frame, and wherein the transformed image frames are input to a trained neural network to determine a layer probability of belonging to an anatomic layer.

8. The method of claim 2, wherein the movement feature extraction and classification step divides the mask into respective segments and classifies the movement features for each of the segments of the corresponding layer, and wherein the associating step associates the classified movement features with the corresponding segments of the layer for the cardiac motion classification.

9. The method of claim 8, further comprising a ventricular insertions location detection step to identify a plurality of ventricular insertions for each image frame, wherein the movement feature extraction and classification step divides the mask into the respective segments based on the ventricular insertions.

10. The method of claim 9, further including a time series calculation step of computing, for each segment of the mask in a pre-determined number of image frames in time, a time series of a tracked deformation feature being at least one of an inner radius of the mask, an outer radius of the mask, an inner curvature of the mask, an outer curvature of the mask, a bloodpool area, and a segment thickness, as an extracted movement feature, and a cardiac motion classifying step of classifying, from the computed time series of the tracked deformation feature, the extracted movement feature into one of the number of pre-determined movement features.

11. The method of claim 2, wherein the movement feature extraction and classification step further comprises:
a first dimensionality reduction step of determining an inner radius and an outer radius of the mask over all angles $\theta$ of the mask from 0° to 360°, and reducing each image frame into a representation defining the inner radius and the outer radius of the mask over the angle $\theta$, and reducing the 4D image data representation of the image frame, $I(x, y, z, t)$, into a first 3D data representation of the image frame, $I(\theta, z, t)$ in which a first image intensity represents a radius value of the inner radius or the outer radius, and
a cardiac motion classifying step of classifying, from the first 3D data representation, an extracted movement feature based on the first image intensity into one of the number of pre-determined movement features.

12. The method of claim 2, wherein the movement feature extraction and classification step further comprises:
a second dimensionality reduction step of determining a deformation direction and/or a deformation magnitude with regard to the mask over all angles $\theta$ of the mask from 0° to 360°, and reducing each image frame into a representation defining the deformation direction and/or the deformation magnitude of the mask over the angle $\theta$, and reducing the 4D image data representation of the image frame, $I(x, y, z, t)$, into a second 3D data representation of the image frame, $I(\theta, z, t)$ in which a second image intensity represents the deformation direction and/or the deformation magnitude, and
a cardiac motion classifying step of classifying, from the second 3D data representation, an extracted movement feature based on the second image intensity into one of the number of pre-determined movement features.

13. The method of claim 1, wherein at least one of the myocardium segmentation step and the slice classification step employs patient data as a direct input or as a normalization component.

14. The method of claim 2, wherein at least one of the movement feature extraction and classification step and the associating step further employs patient data as a direct input or as a normalization component.

15. The method of claim 1, wherein each of the myocardium segmentation step and the slice classification step is performed using at least one deep neural network.

16. The method of claim 2, wherein each of the movement feature extraction and classification step is performed using at least one deep neural network.

17. The method of claim 15, further comprising a post-processing step for incorporating at least one of spatial and temporal coherence of output predictions in the at least one deep neural network.

18. The method of claim 15, further comprising a post-processing step of creating a plurality of versions of an image frame of the plurality of image frames and applying the plurality of versions to the deep neural network.

19. The method of claim 18, wherein the plurality of versions of the image frame is created by transforming the image frame.

20. The method of claim 18, wherein the output of the at least one deep neural network with regard to the inputted plurality of versions of the image frame is averaged.

* * * * *